(12) United States Patent  
Axelson, Jr. et al.

(10) Patent No.: US 8,821,507 B2  
(45) Date of Patent: Sep. 2, 2014

(54) AUGMENTATION DELIVERY DEVICE

(75) Inventors: Stuart L. Axelson, Jr., Succasunna, NJ (US); Damon Servidio, Towaco, NJ (US); Jon B. Tucker, Presto, PA (US); Jeffrey Kapec, Westport, CT (US); Yoshi Matsuda, New York, NY (US); Yukiko Naoi, New York, NY (US); Kazuna Tanaka, Cos Cob, CT (US); Richard M. Seldes, Rockleigh, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1399 days.

(21) Appl. No.: 11/825,662

(22) Filed: Jul. 6, 2007

(65) Prior Publication Data

US 2009/0012521 A1    Jan. 8, 2009

(51) Int. Cl.
*A61B 17/56* (2006.01)
*A61F 2/00* (2006.01)
*A61B 17/00* (2006.01)
*A61B 17/34* (2006.01)
*A61F 2/08* (2006.01)

(52) U.S. Cl.
CPC ......... *A61B 17/00234* (2013.01); *A61F 2/0063* (2013.01); *A61B 17/0057* (2013.01); *A61B 17/3417* (2013.01); *A61F 2/08* (2013.01); *A61B 2017/3482* (2013.01); *A61F 2002/0072* (2013.01)
USPC .............................................. 606/99; 606/14

(58) Field of Classification Search
USPC ........................................ 606/1.15, 13, 14, 99
See application file for complete search history.

(56) References Cited

U.S. PATENT DOCUMENTS

| | | | | | |
|---|---|---|---|---|---|
| 1,275,520 | A | * | 8/1918 | Bell | 600/206 |
| 3,586,243 | A | * | 6/1971 | Jones | 239/492 |
| 3,818,511 | A | * | 6/1974 | Goldberg et al. | 623/1.31 |
| 3,857,395 | A | | 12/1974 | Johnson et al. | |
| 4,665,906 | A | * | 5/1987 | Jervis | 606/78 |
| 4,706,316 | A | * | 11/1987 | Tanzi | |
| 4,741,330 | A | | 5/1988 | Hayhurst | |
| 5,290,305 | A | * | 3/1994 | Inoue | 623/1.2 |
| 5,304,187 | A | | 4/1994 | Green et al. | |
| 5,334,217 | A | * | 8/1994 | Das | 606/213 |
| 5,370,650 | A | * | 12/1994 | Tovey et al. | 606/151 |
| 5,395,383 | A | | 3/1995 | Adams et al. | |
| 5,397,332 | A | * | 3/1995 | Kammerer et al. | 606/151 |
| 5,405,360 | A | | 4/1995 | Tovey | |
| 5,417,691 | A | | 5/1995 | Hayhurst | |
| 5,503,623 | A | | 4/1996 | Tilton, Jr. | |
| 5,554,163 | A | * | 9/1996 | Shturman | 606/159 |
| 5,601,557 | A | | 2/1997 | Hayhurst | |

(Continued)

*Primary Examiner* — Christian Sevilla
(74) *Attorney, Agent, or Firm* — Lerner, David, Littenberg, Krumholz & Mentlik, LLP (57) ABSTRACT

The tissue augment sheet delivery system includes a tube funnel adapter and a tissue augment sheet delivery instrument. The tube funnel adapter includes a oval/conical shaped funnel. The tissue augment sheet delivery instrument includes a handle. A cylindrical tube is connected to the handle. A wire is inserted in the tube. The wire is formed in a large loop with small loops formed in the large loop. A tissue augment sheet is attached to one side of the large loop using a monofilament. In use, the tube funnel adapter is inserted in body. The tissue augment sheet is placed in mouth of the oval/conical shaped funnel and gently moved down. While moving down, the tissue augment sheet conforms to the internal diameter of the tube funnel adapter. The handle is withdrawn to remove the large loop from the body leaving the tissue augment sheet in body.

25 Claims, 10 Drawing Sheets

(56) References Cited

U.S. PATENT DOCUMENTS

| | | |
|---|---|---|
| 5,647,874 A | 7/1997 | Hayhurst |
| 6,042,610 A * | 3/2000 | Li et al. ...................... 623/20.32 |
| 6,193,731 B1 | 2/2001 | Oppelt et al. |
| 6,200,336 B1 | 3/2001 | Pavcnik et al. |
| 6,428,546 B1 | 8/2002 | Cancel et al. |
| 6,656,182 B1 | 12/2003 | Hayhurst |
| 2003/0216747 A1 * | 11/2003 | Kaplan ........................ 606/107 |
| 2004/0087907 A1 * | 5/2004 | Smith et al. .................. 604/228 |
| 2004/0249442 A1 * | 12/2004 | Fleming et al. .............. 623/1.15 |

* cited by examiner

AUGMENTATION DELIVERY DEVICE

BACKGROUND OF THE INVENTION

1. Field of the Invention

The present invention relates to an apparatus for inserting surgical material in the body. In particular the present invention relates to a delivery apparatus for a tissue augment that may be in form of a sheet to repair a tissue such as rotator cuff, bicep or quadriceps.

2. Description of Related Art

In order to repair a torn rotator cuff, the surgeons reattach the damaged tendon or tendons to the upper arm or humerus. For challenging tendon repair surgery, surgeons need a strong, suturable scaffold (i.e., tissue augment) to augment the repair both physically and biologically. Tissuemend® is an example of a suitable tissue augment sheet. Tissuemend® is a remodelable collagen scaffold derived from bovine skin to be used to reinforce soft tissue where weakness exists. It is specifically designed to serve as a scaffold for cellular and vascular ingrowth that is gradually remodeled into new tissue.

Surgical procedures such as shoulder rotator cuff repair with tissue augmentation are performed with traditional open, mini-open, and arthroscopic surgical technique. There are advantages to arthroscopic procedures over traditional open or mini-open procedures mostly due to improved visualization. Arthroscopic surgery is a technique for performing an operation using pen-shaped instruments with a miniature video camera attached to the end. Because arthroscopic surgery requires only limited surgical access, the incision is much smaller than is necessary for open surgery, resulting in fewer risks. The patient's recovery time is also shorter.

Current arthroscopic surgical procedures using tissue augmentation are higher cost due to prolonged surgical time. Surgical techniques are not user friendly requiring increased surgeon training to master the technique. Causes may range from difficult placement of augmentation tissue, challenging suturing technique and suture management. Many tissue augmentation products do not offer specifically designed arthroscopic instruments for implantation.

However, some applicators for applying surgical materials are known in the art. Conventional applicators require folding of the material that is to be inserted in the body cavity and then unfolding of the same inside the body cavity. Tightly folded sheet materials are difficult and time consuming to unfold.

U.S. Pat. No. 5,503,623 (the '623 patent) is directed at a method and apparatus for laparoscopic insertion and application of sheet like surgical material. To introduce and apply a large sheet like material, the '623 patent provides a method and apparatus of grasping and furling the sheet and then unfurling, releasing and applying it after passage into the patient's abdominal cavity. The apparatus consists of a grasping and furling portion which is rotated to furl the sheet like material. The furled material is then drawn into a tubular portion of the instrument. The tubular portion is introduced in the body through a valved port. Once the sheet like material is in the abdominal cavity it is unfurled. The need for furling and unfurling makes the process of insertion of the material complex, time consuming and prone to error.

U.S. Pat. No. 5,405,360 discloses an apparatus for positioning surgical implants adjacent to body tissue. The apparatus has a delivery device having a plurality of delivery arms positioned at the distal end of an elongated rod. A surgical implant is releasably secured to the delivery arms by a securing device such as sutures. The invention also provides a method for positioning surgical implants adjacent to body tissue. The apparatus uses a pusher rod to properly unfurl the surgical material being implanted.

Therefore, there is a need for a simple, easy to use tissue augment delivery system that allows accurate and fast placement of the scaffold.

SUMMARY OF THE INVENTION

The present invention provides a tissue augment sheet delivery system. The tissue augment sheet delivery system includes a tube funnel adapter and a tissue augment sheet delivery instrument. Tube funnel adapter includes a oval/conical shaped funnel. A circular end of the oval/conical shaped funnel is connected to a circular end of a cylindrical extension of a barrel portion. The barrel portion has a cylindrical tube connected at the end opposing circular end. The tissue augment sheet delivery instrument includes a handle. A first cylindrical tube is connected to the handle. A second cylindrical tube is attached along the longitudinal axis of the primary cylindrical tube. A wire is inserted in the first cylindrical tube. The wire is formed in a large loop with small loops formed within the large loop. A tissue augment sheet is attached to one side of the large loop using a monofilament. The monofilament loop extends from the tissue augment sheet and is drawn proximal from the tissue augment sheet through the second cylindrical tube and brought up to the handle. The monofilament may be held in tension during application by means of a plastic locking feature that is formed in the handle. After the tissue augment sheet is delivered it is released by cutting the monofilament loop distally at the tissue augment sheet.

In use, the tube funnel adapter is inserted into a working cannula which is inserted into the body of the patient and the tissue augment sheet delivery instrument is positioned above the mouth of the oval/conical shaped funnel. The tissue augment sheet is placed in the mouth of the oval/conical shaped funnel and gently moved down. By virtue of the oval/conical shape of the funnel, the "S" shaped neck on the handle, and the fact that the plane of the large loop is tilted with respect to the longitudinal axis of the handle, the tissue augment sheet aligns itself with the longitudinal axis of the oval/conical shaped funnel as it is moved further in the oval/conical shaped funnel. As the tissue augment sheet moves further along the longitudinal axis, the large loop collapses to the size of the internal diameter of the passage extending from the mouth of the oval/conical shaped funnel to the tip of the cylindrical tube that is farthest from the mouth. While traveling through the passage extending from the mouth of the oval/conical shaped funnel to the tip of the cylindrical tube, the tissue augment sheet conforms to the internal diameter of the tube funnel adapter. Upon exiting the tube funnel adaptor inside the body, for example, in the rotator cuff, large loop expands to regain its shape and the tissue augment sheet is deployed. The handle is withdrawn (after the monofilament loop has been cut and drawn up through the second tube) to remove the large loop from the body leaving the tissue augment sheet in place.

DETAILED DESCRIPTION

Figure 1:
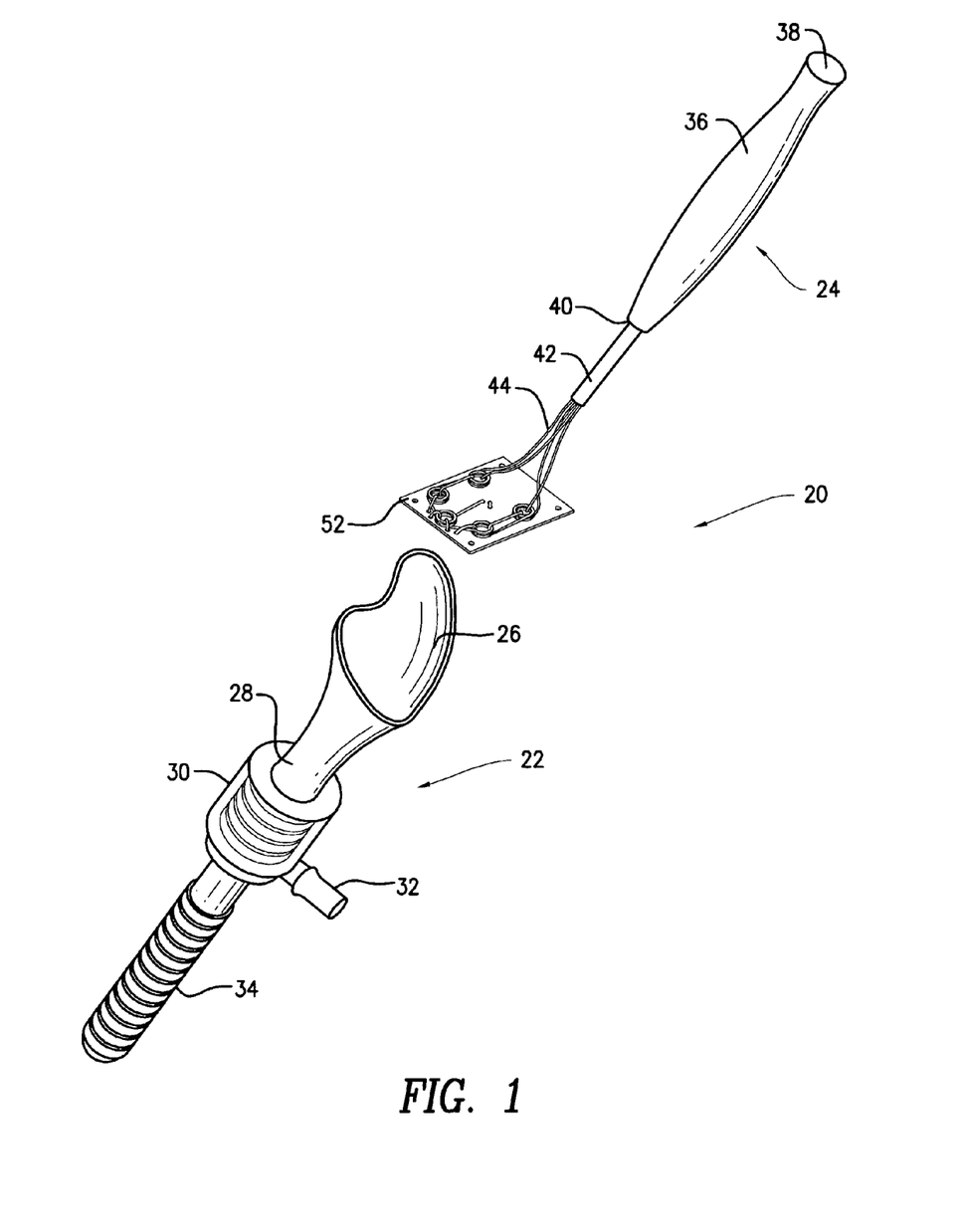
FIG. 1 shows a tissue augment sheet delivery system.
Figure 4:
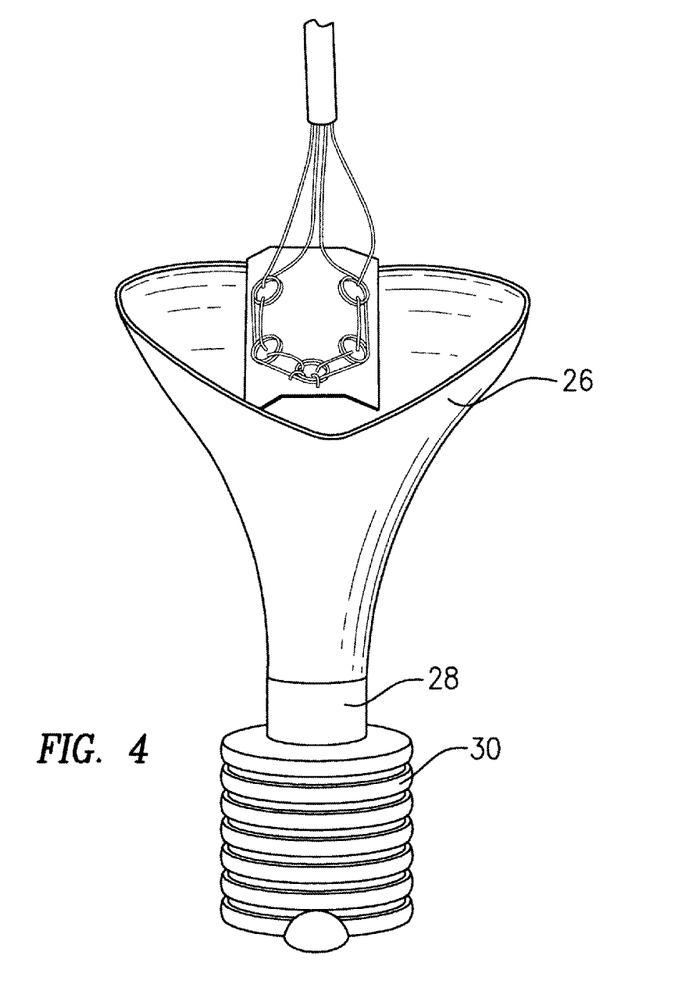
FIG. 4 shows an isometric view of an oval/conical shaped funnel attached to a barrel portion and a delivery instrument placed in the mouth of the funnel.

FIG. 1 shows a tissue augment sheet delivery system 20. Tissue augment sheet delivery system 20 includes a tube funnel adapter 22 and a tissue augment sheet delivery instrument 24. Tube funnel adapter 22 and tissue augment sheet delivery instrument 24 may be disposable. Tube funnel adapter 22 includes a oval/conical shaped funnel 26 (i.e., funnel 26 is approximately oval as seen in an end view and funnel shaped along its longitudinal axis). The mouth of oval/conical shaped funnel 26 is oval and tapers in a conical manner to an opposing end that is circular (see FIG. 4). Oval/conical shaped funnel 26 gradually transitions from the oval/conical shape near the mouth to the circular shape along the longitudinal axis of oval/conical shaped funnel 26. The circular end of oval/conical shaped funnel 26 is connected to a circular end 28 of a cylindrical extension of a barrel portion 30. The longitudinal axes of barrel portion 30, circular end 28 and oval/conical shaped funnel are substantially aligned. A cylindrical tube 32 is connected to the outer wall of barrel portion 30. The longitudinal axis of cylindrical tube 32 is orthogonal to the longitudinal axis of barrel portion 30. Barrel portion 30 has a cylindrical tube 34 connected at the end opposing circular end 28. The longitudinal axis of cylindrical tube 34 is substantially aligned with the longitudinal axis of barrel portion 30. Cylindrical tube 34 may have a corrugated surface. Cylindrical tube 34 aligns oval/conical funnel 26 with the longitudinal axis of a cannula (not shown in Figures) and serves as a means of structural engagement between the cannula and funnel 26. Cylindrical tube 34 also permits passage through a membrane seal (not shown in Figures) that is present in the cannula. If this membrane seal is not opened before a tissue augment sheet 52 (FIGS. 2 and 9) is introduced down funnel 26, the tissue augment sheet 52 would not pass beyond the seal.

Figure 2:
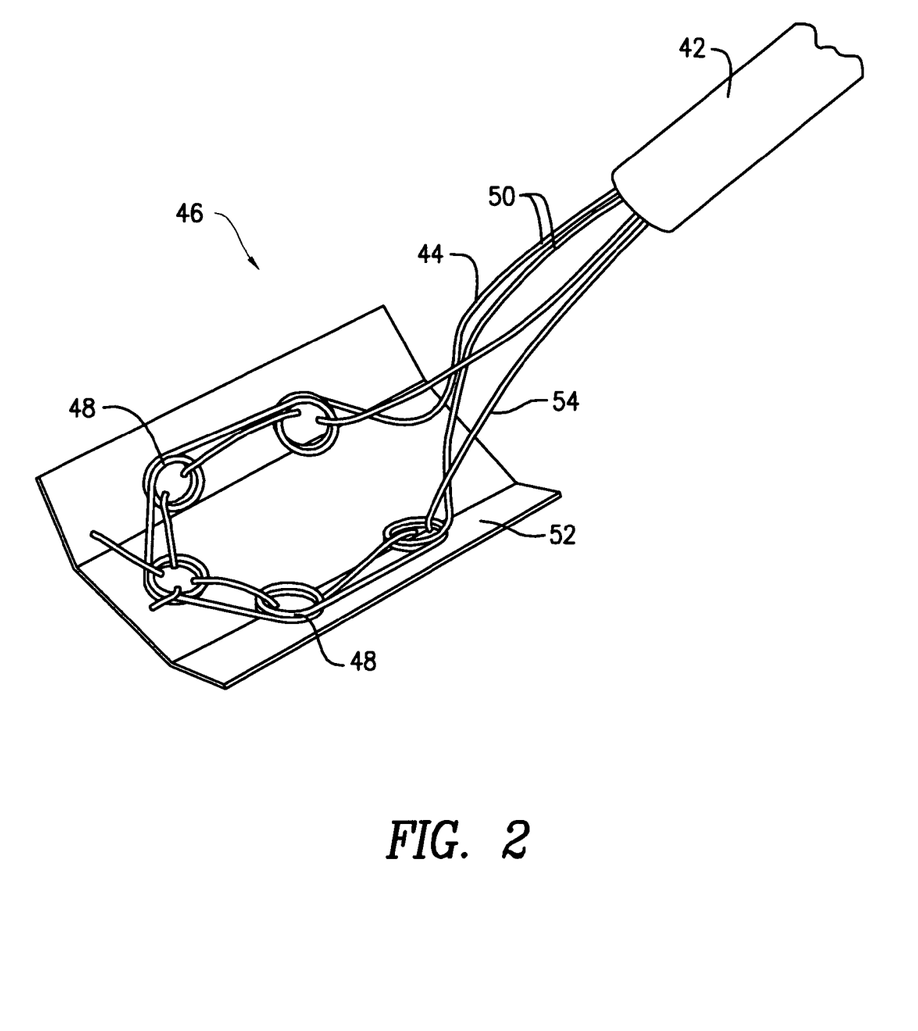
FIG. 2 shows a tissue augment sheet attached to one end of a tissue augment sheet delivery instrument used in system of FIG. 1.
Figure 5:
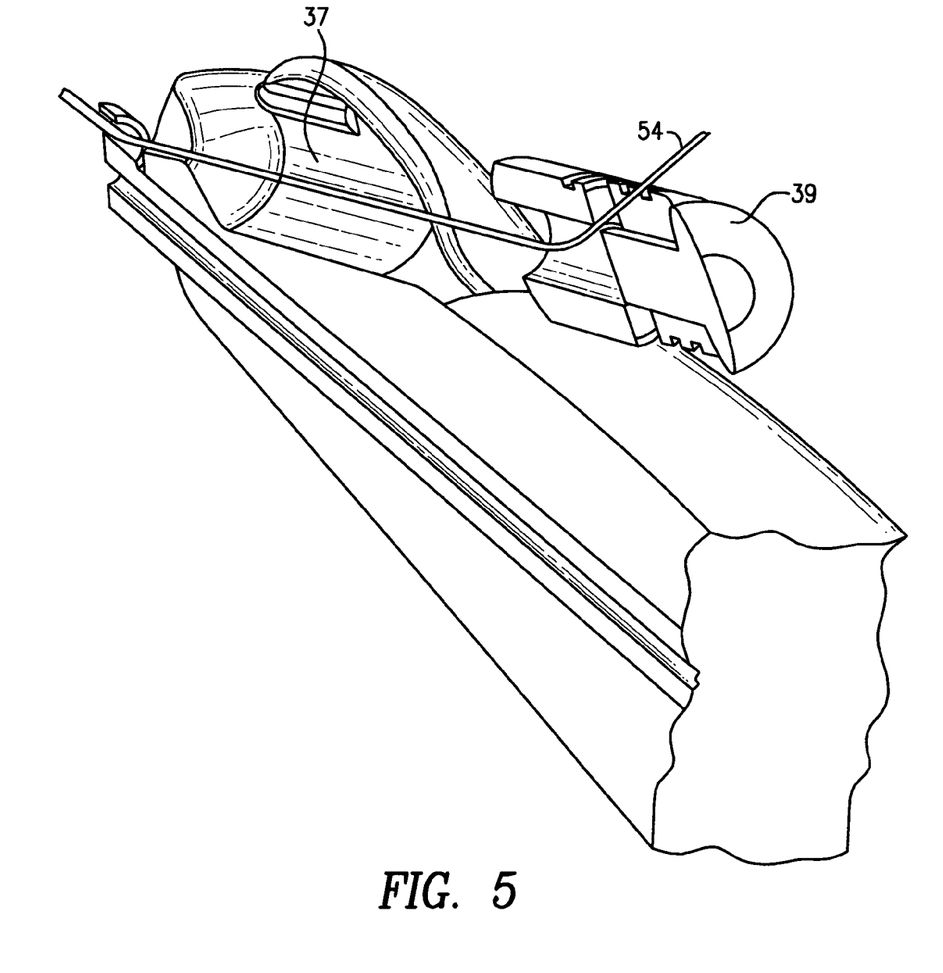
FIG. 5 is a drawing showing an embodiment of a handle of a delivery instrument for use with the tissue augment sheet delivery system of FIG. 1.
Figure 11:
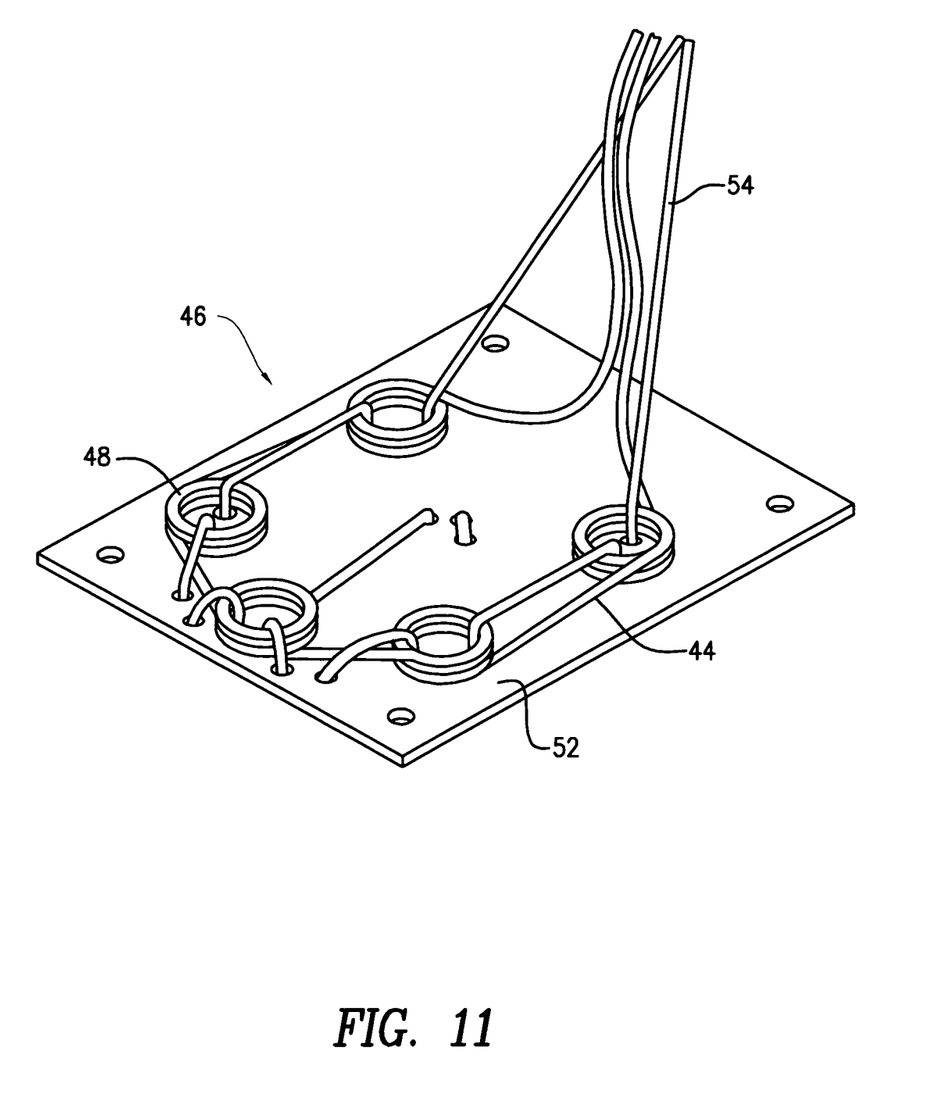
FIG. 11 shown another embodiment of a tissue augment sheet having holes for attachment to the tissue.

Tissue augment sheet delivery instrument 24 includes a handle 36. Handle 36 has a first end 38 and a second end 40. In one embodiment (FIG. 5), handle 36 has a recess 37 that contains a plastic locking feature 39 that holds a monofilament 54 into a static position during delivery and positioning of the tissue augment sheet 52. Handle 36 may be made from any suitable material. A cylindrical tube 42 is connected to second end 40. A wire 44 is inserted in tube 42. Wire 44 forms a large loop 46 (FIGS. 2 and 11). Large loop 46 is formed by inserting both ends of wire 44 in cylindrical tube 42. Small loops 48 are also formed in large loop 46. Small loops 48 may be formed by bending wire 44 in a circular shape along length of large loop 46. Wire 44 may be made from, for example, surgical grade spring, stainless steel or Nitinol or similar type of spring wire. Large loop 46 may be substantially polygonal in shape and be capable of flexing. The smaller loops aid in the flexure of the larger loop. The smaller spring loops formed within the larger loop permit the larger loop to substantively collapse into a compact shape which will compress through the oval/conical shaped funnel 26 and through the cylindrical tube 34. Flexing and compression of the larger loop is further enhanced by the "S" shaped neck which is comprised of two wire segments which deflect apart when the large loop is compressed through the funnel 26. Sections 50 of wire 44 connect large loop 46 to cylindrical tube 42. The portions of sections 50 that form the large loop 46 are bent such that the plane of loop 46 is tilted with respect to the longitudinal axis of handle 36 (see FIGS. 1 and 2). The shape of large loop 46 and its angle relative to longitudinal axis of handle 36 forces the tissue augment sheet 52 to eject from the distal end of the cannula in a very confined space. Without this feature the tissue augment sheet 52 would not be able to pass beyond the distal tip of the cannula.

Figure 6:
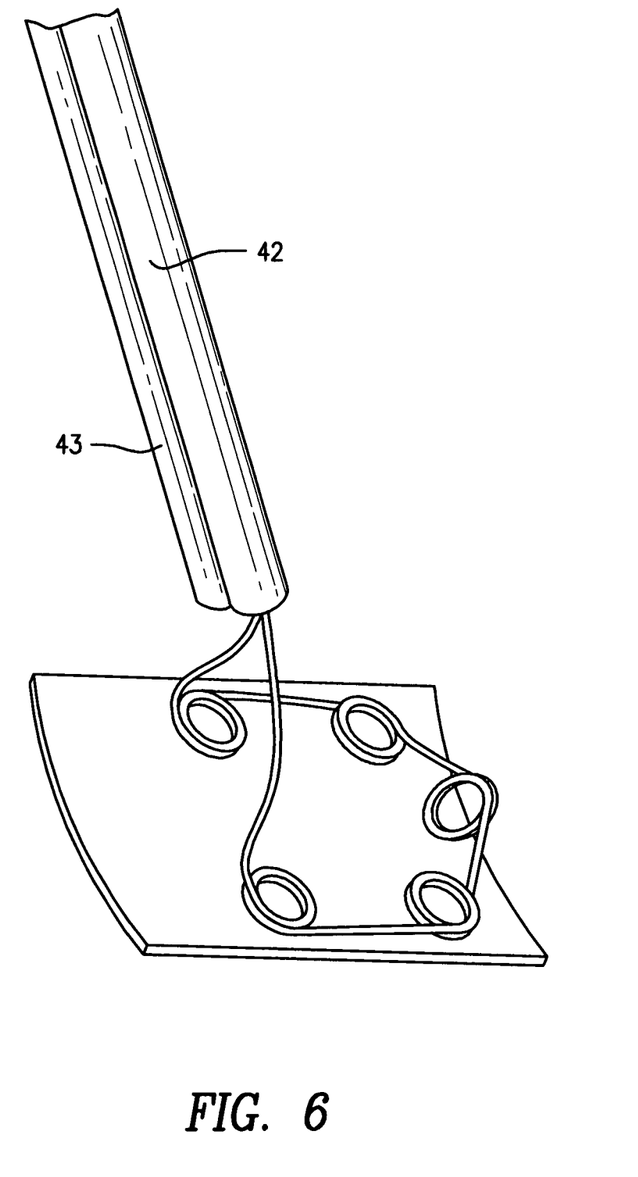
FIG. 6 is a drawing showing a tissue augment sheet attached to one end of a tissue augment sheet delivery instrument for use in the system of FIG. 1.
Figures 7, 8:
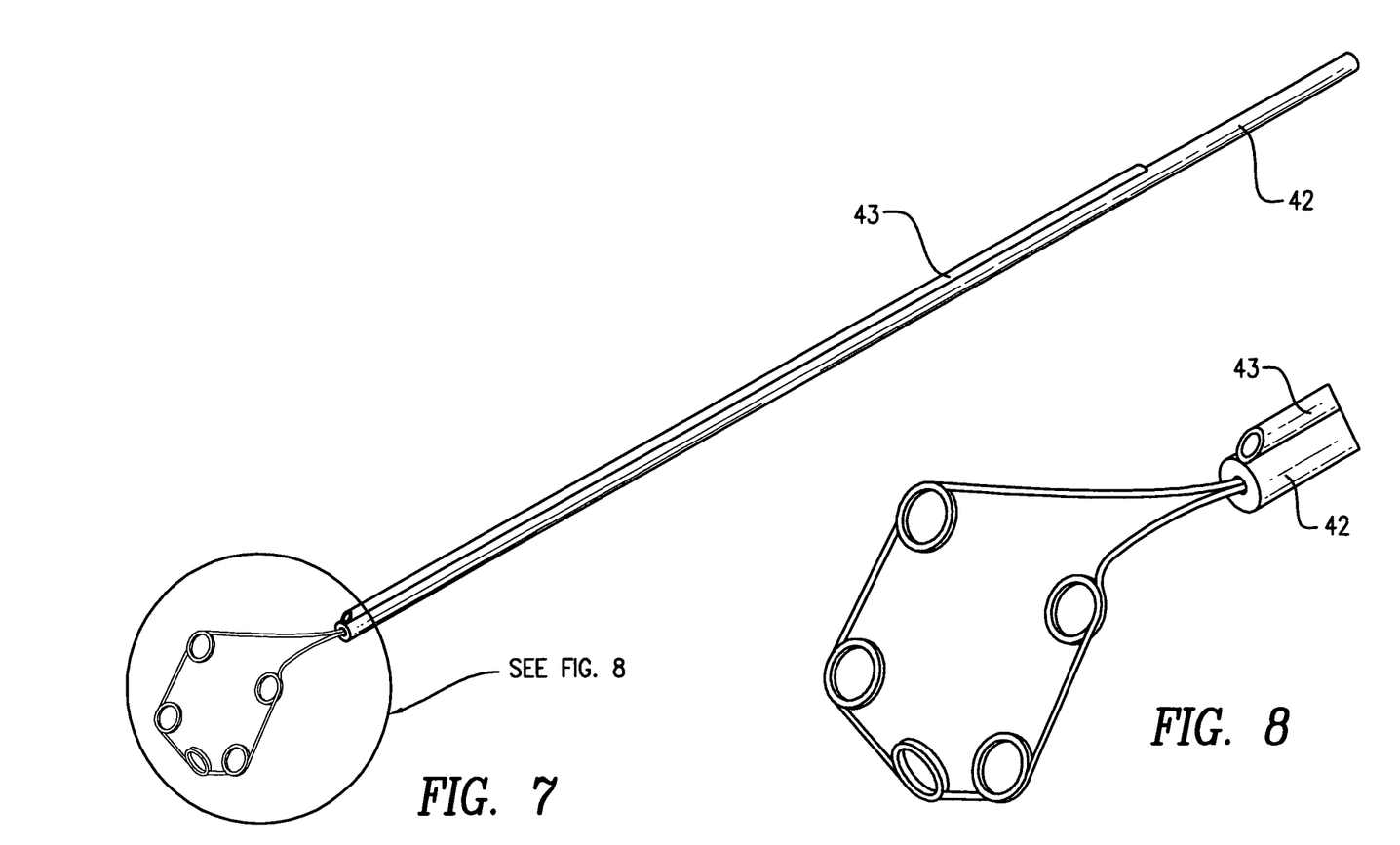
FIG. 7 is an isometric view showing a tissue augment sheet delivery instrument for use in the system of FIG. 1.
FIG. 8 is an isometric view of a portion of tissue augment sheet delivery instrument of FIG. 7 showing a large loop attached to the handle via an "S" shaped neck portion.
Figure 10:
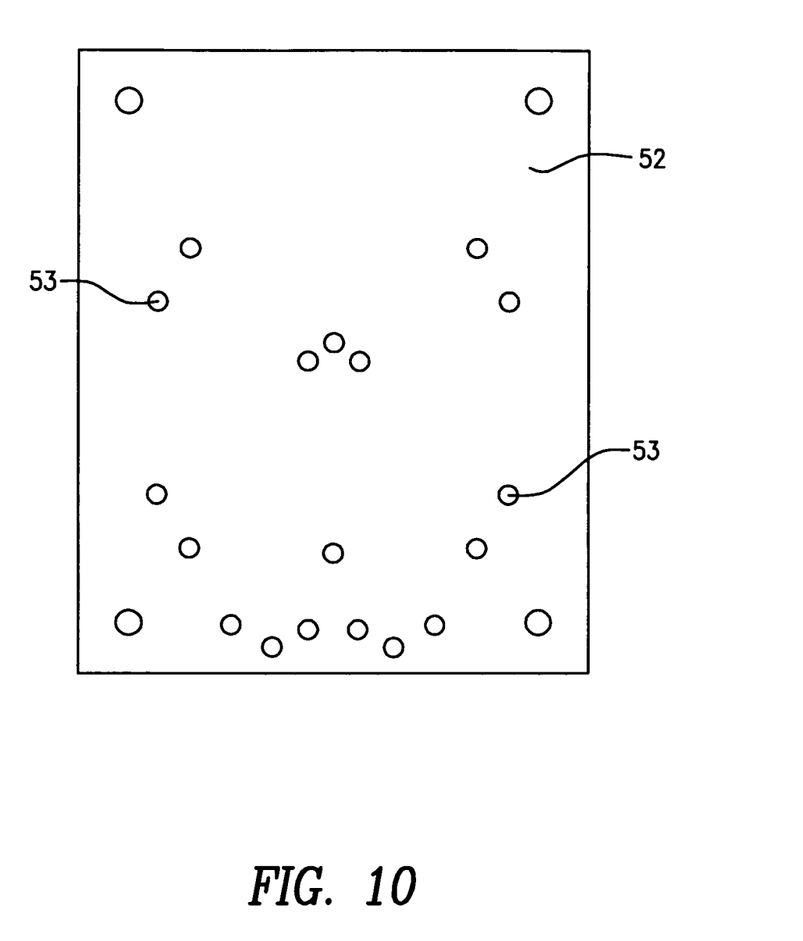
FIG. 10 is an isometric view of another embodiment of a tissue augment sheet attached to one end of a tissue augment sheet delivery instrument.

The tissue augment sheet 52 is attached to one side of large loop 46. To attach tissue augment sheet 52 to large loop 46, tissue augment sheet 52 is placed under large loop 46 and a monofilament (or a suture) 54 is passed through small loops 48. The ends of monofilament 54 may exit next to cylindrical tube 42 or may enter through a second cylindrical tube 43 (FIGS. 6, 7 and 8) positioned parallel to the primary cylindrical tube 42 and exit from handle 36. This method of attaching tissue augment sheet is very robust and tolerates pulling and pushing. To release tissue augment sheet 52 from the large loop 46, the surgeon would cut end of monofilament 54 and pull on the end of monofilament 54 to pull it through small loops 48. Tissue augment sheet 52 may be made from collagen scaffold such as Tissuemend®. Tissue augment sheet may include means for suture attachment such as suture holes 53 (FIG. 10). Suture holes 53 may be coded, for example color coded, to help identify the proper orientation of the suture relative to attachment to the appropriate rotator cuff anatomy. Tissue augment sheet 52 may include embedded within it a web of suture material to provide added rigidity.

Figure 3:
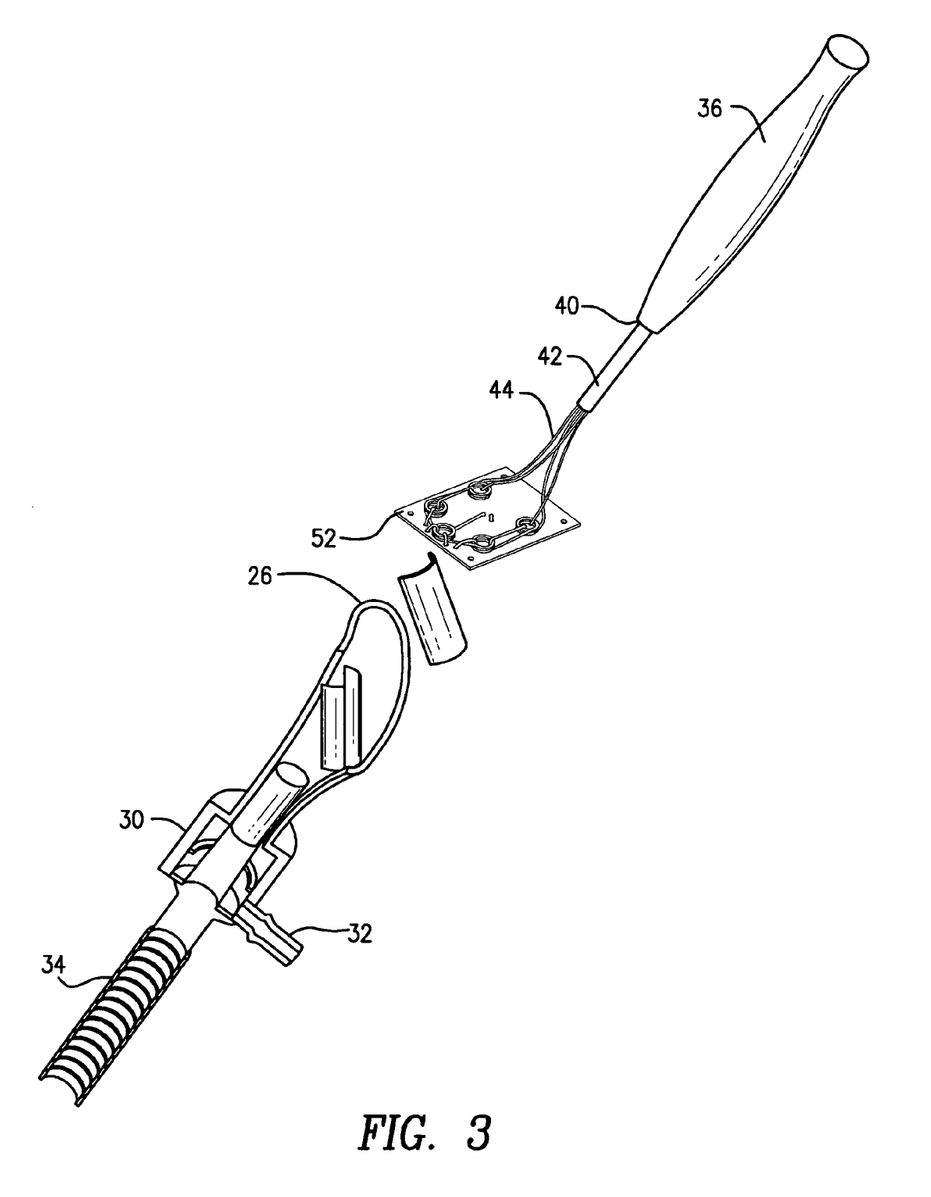
FIG. 3 is a partial cross-sectional view of tissue augment sheet delivery system of FIG. 1 showing the tissue augment sheet of FIG. 2 at various stages of its travel through the tube funnel adapter used in FIG. 1.
Figure 9:
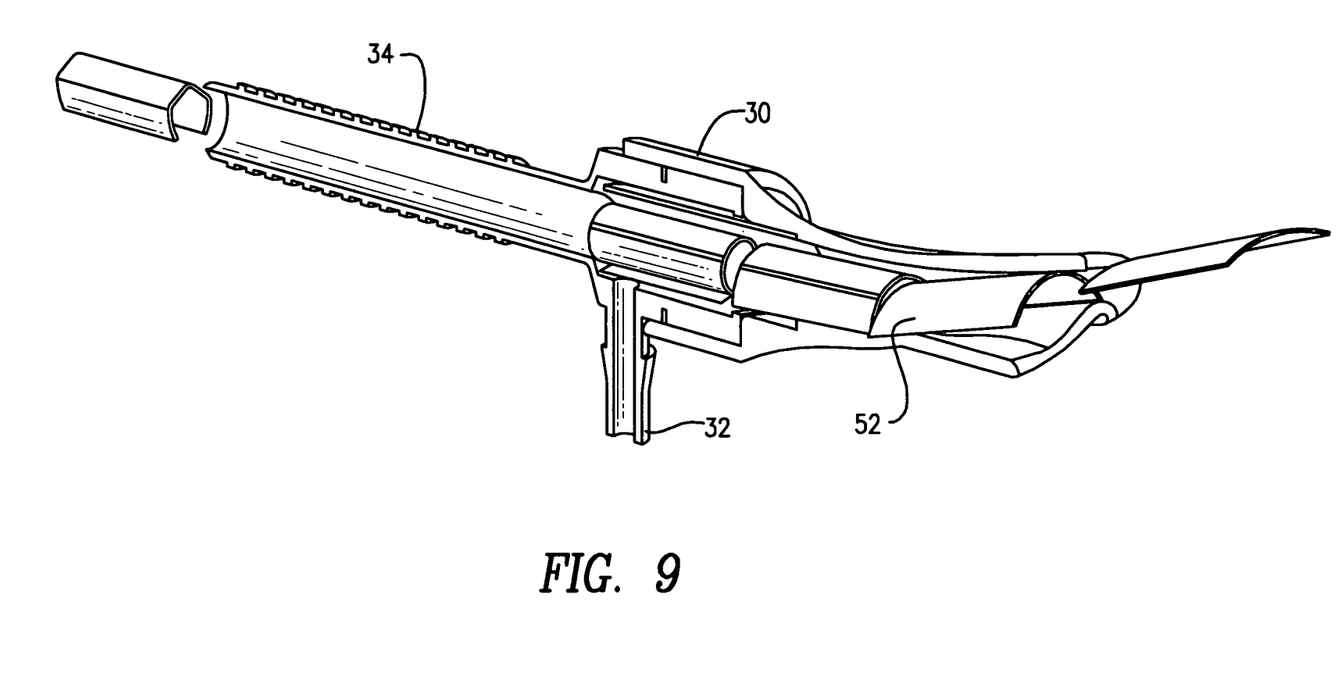
FIG. 9 is a drawing showing in a cut away view of the tissue augment sheet in various stages of travel through the tissue augment sheet delivery system.

FIGS. 3 and 9 shows tissue augment sheet 52 at various points of insertion in tube funnel adapter 22. In use, tube funnel adapter 22 is inserted in a cannula which is inserted in the body. The tissue augment sheet delivery instrument 24 is positioned above the mouth of oval/conical shaped funnel 26. Tissue augment sheet 52 mounted on large loop 46 is placed in mouth of oval/conical shaped funnel 26 and gently moved down. By virtue of the oval/conical shape and the fact that the plane of large loop 46 is tilted with respect to the longitudinal axis of handle 36, tissue augment sheet 52 aligns itself with the longitudinal axis of oval/conical shaped funnel 26 as it is moved further in oval/conical shaped funnel 26. As tissue augment sheet 52 moves further along the longitudinal axis, large loop 46 collapses to the size of the internal diameter of the passage extending from the mouth of oval/conical shaped funnel 26 to the tip of cylindrical tube 34 that is farthest from the mouth. The collapsing of large loop 46 is aided by the presence of small loops 48. Collapsing may be further aided by the paired wire section that forms the "S" shaped neck. While traveling through the passage extending from the mouth of oval/conical shaped funnel 26 to the tip of cylindrical tube 34, tissue augment sheet 52 conforms to the internal diameter of tube funnel adapter 22. Thus, tissue augment sheet 52 is not folded for transportation to the site of implantation. Upon exiting tube funnel adaptor 22 inside the body, for example, in the rotator cuff, loop 46 flips out of the tip of the cannula and expands within the very confined space to regain its shape and tissue augment sheet 52 is deployed. The "S" shape of the wire form (i.e., the neck) that extends from the tube and connects to the large loop results in the tissue augment being flipped into a functional position once the tissue augment exits beyond the distal tip of the cannula. The "S" shaped neck functions as an articulation spring and permits the tissue augment to be deployed onto the rotator cuff in the very confined space of this anatomy. Without this specific feature it would be impossible to open the full shape of the augment in such limited confines. At this time the surgeon may manipulate handle 36 to position tissue augment sheet 52 in desired position. Next the surgeon cuts monofilament 54 and pulls on its end to remove monofilament 54 and leave tissue augment sheet 52 in the desired location. Next, handle 36 is withdrawn to remove loop 46 from the body leaving tissue augment sheet 52 in place.

In an alternative embodiment, tissue augment sheet 52 is pre-assembled into a delivery cartridge sized to pass through a cannula. The cartridge automatically opens once inside the joint or soft tissue space. The cartridge may be disposable.

In yet another embodiment, a pre-loaded "memory loop" spring frame is embedded within tissue augment sheet 52 instead of large loop 46. Tissue augment sheet 52 may also include means for suture attachment such as suture holes 53. Tissue augment sheet 52 may also include a web of suture material to provide added dimensional rigidity.

The embodiments described above provide a simple, easy to use, specifically designed scaffold delivery device resulting in less operating room confusion and reduced surgical time due to accurate placement and fixation of scaffold such as Tissuemend®. Surgeon training is reduced leading to superior confidence and control.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tissue augment sheet delivery system comprising:
a wire frame having at least one loop;
a tissue augment sheet attached to the wire frame by a monofilament;
a handle attached to the wire frame extending along a longitudinal handle axis;
a longitudinal tube adjacent the handle and extending parallel to the longitudinal handle axis, at least a portion of the monofilament capable of passing through the longitudinal tube; and
a tube funnel adaptor comprising a funnel and a funnel tube attached to the funnel, the funnel tube extending along a longitudinal funnel axis, and the funnel comprising a first exposed open end having a first width and an opposed second end having a second width less than the first width, wherein a widest portion of the funnel is at the first exposed open end, the widest portion of the funnel having a first shape that is gradually reduced in a conical manner to a second shape, and the second shape matching an internal diameter of the funnel tube,
wherein the wire frame compresses to pass through the tube funnel adaptor, wherein a plane of the at least one loop is angled relative to the longitudinal funnel axis so as to cause the wire frame to collapse and the tissue augment sheet attached to the wire frame to be aligned with the longitudinal funnel axis when the wire frame passes through the tube funnel adaptor, and wherein the tissue augment sheet conforms to an internal space of the tube funnel adaptor.

2. The tissue augment sheet delivery system of claim 1, wherein the first shape of the funnel is an oval/conical shape.

3. The tissue augment sheet delivery system of claim 2, wherein the tube funnel adaptor is disposable.

4. The tissue augment sheet delivery system of claim 1, wherein the widest portion of the funnel has an oval shape.

5. The tissue augment sheet delivery system of claim 4, wherein the wire frame is made from a material selected from a group consisting of surgical grade stainless steel wire, spring wire and nitinol.

6. The tissue augment sheet delivery system of claim 5, wherein the wire frame has five loops.

7. The tissue augment sheet delivery system of claim 6, wherein the wire frame is attached to the handle via a "S" shaped neck portion configured to allow further compression of the wire frame and to make the wire frame flip open upon exiting the tissue augment sheet delivery system.

8. The tissue augment sheet delivery system of claim 7, wherein the tissue augment sheet delivery system is disposable.

9. The tissue augment sheet delivery system of claim 6, wherein the monofilament passes through at least one loop.

10. The tissue augment sheet delivery system of claim 9, wherein the monofilament holds the tissue augment sheet to the wire frame, and the monofilament is configured to slide out leaving the tissue augment sheet in place.

11. The tissue augment sheet delivery system of claim 9, wherein the tissue augment sheet has openings for suture attachment.

12. The tissue augment sheet delivery system of claim 11, wherein the openings for suture attachment are color coded.

13. The tissue augment sheet delivery system of claim 6, wherein the tissue augment sheet includes a web of suture material.

14. The tissue augment sheet delivery system of claim 9, wherein the tissue augment sheet is made from collagen scaffold.

15. A method of implanting a tissue augment material, the method comprising the steps of:
inserting a tube funnel adapter in a body of a patient, the tube funnel adapter comprising a funnel and a funnel tube attached to the funnel, the funnel comprising a first exposed open end having a first width and a second end having a second width less than the first width, and wherein a widest portion of the funnel of the tube funnel adapter is at the first exposed open end;
attaching a tissue augment sheet to a tissue augment delivery instrument with a monofilament, the tissue augment delivery instrument including a handle extending along a longitudinal axis and a longitudinal tube extending parallel to the longitudinal axis;
passing at least a portion of the monofilament through the longitudinal tube;
positioning the tissue augment sheet attached to the tissue augment delivery instrument at the first exposed open end of the tube funnel adaptor;
moving the tissue augment delivery instrument and the tissue augment sheet through the tube funnel adaptor so as to cause the augment delivery instrument to collapse and the tissue augment sheet to be aligned with and conformed to an internal diameter of the tube funnel adapter during the insertion of the tissue augment delivery instrument; and withdrawing the tissue augment delivery instrument from the body leaving the tissue augment sheet in the body.

16. The method of claim 15, further comprising the step of: attaching the tissue augment sheet to the body using openings provided in the tissue augment sheet.

17. The method of claim 16, wherein the openings are color coded.

18. The method of claim 16, further comprising the step of: disposing the tissue augment delivery instrument and the tube funnel adapter.

19. The tissue augment sheet delivery system of claim 1, wherein the wire frame is attached to the handle via a "S" shaped neck portion wherein the "S" shaped neck portion is comprised of at least two wires capable of deflecting apart when the wire frame is compressed through the funnel.

20. The tissue augment sheet delivery system of claim 19, wherein the "S" shaped neck portion is adapted to make the wire frame flip open upon exiting the tissue augment sheet delivery system.

21. The tissue augment sheet delivery system of claim 1, wherein the wire frame further includes a first loop and a second loop, wherein the second loop is formed within the first loop.

22. The method of claim 15, wherein the widest portion of the funnel has a first shape that is gradually reduced in a conical manner to a second shape at its second end.

23. The tissue augment sheet delivery system of claim 1, wherein the funnel further comprises an outer surface, an inner surface, and a top edge at the first exposed open end extending between the outer surface and inner surface.

24. The tissue augment sheet delivery system of claim 1, wherein when the tissue augment sheet and tissue augment delivery instrument is positioned at the first exposed open end of the tube funnel adaptor, the tissue augment delivery instrument is in an open or expanded state.

25. The method of claim 15, further including the step of attaching the tissue augment delivery sheet to the tissue augment delivery instrument prior to positioning the tissue augment delivery instrument at the first exposed end of the tube funnel adaptor.

* * * * *